United States Patent
Carol

(10) Patent No.: US 10,111,716 B2
(45) Date of Patent: Oct. 30, 2018

(54) SYSTEM FOR AND METHOD OF PERFORMING SONASURGERY

(71) Applicant: SONACARE MEDICAL, LLC, Charlotte, NC (US)

(72) Inventor: Mark Carol, Charlotte, NC (US)

(73) Assignee: SONACARE MEDICAL, LLC NC (US)

( * ) Notice: Subject to any disclaimer, the term of this patent is extended or adjusted under 35 U.S.C. 154(b) by 269 days.

(21) Appl. No.: 15/027,048

(22) PCT Filed: Oct. 10, 2014

(86) PCT No.: PCT/US2014/060066
§ 371 (c)(1),
(2) Date: Apr. 4, 2016

(87) PCT Pub. No.: WO2015/054592
PCT Pub. Date: Apr. 16, 2015

(65) Prior Publication Data
US 2016/0235484 A1 Aug. 18, 2016

Related U.S. Application Data

(60) Provisional application No. 61/889,863, filed on Oct. 11, 2013.

(51) Int. Cl.
*A61B 34/20* (2016.01)
*A61B 34/00* (2016.01)
(Continued)

(52) U.S. Cl.
CPC ................ *A61B 34/20* (2016.02); *A61B 8/12* (2013.01); *A61B 17/00234* (2013.01);
(Continued)

(58) Field of Classification Search
CPC ......... A61B 34/20; A61B 34/76; A61B 34/30; A61B 2034/2055; A61B 2034/2063;
(Continued)

(56) References Cited

U.S. PATENT DOCUMENTS 6,298,262 B1 * 10/2001 Franck .................. A61B 90/11
600/426
6,301,495 B1 10/2001 Gueziec et al.
(Continued)

FOREIGN PATENT DOCUMENTS

| CN | 2857869 Y | 1/2007 |
|---|---|---|
| CN | 102905642 A | 1/2013 |

(Continued)

OTHER PUBLICATIONS

Extended European Search Report dated Jul. 11, 2017 for European Patent Application No. 14852021.6.
(Continued)

*Primary Examiner* — Katrina Stransky
(74) *Attorney, Agent, or Firm* — Mark T. Vogelbacker; Eckert Seamans Cherin & Mellott LLC

(57) ABSTRACT

An apparatus for and a method of performing sonasurgery may include a room coordinate system and at least one probe with localization technology. A position of the probe may be tracked continuously during the course of a procedure so that its position is known and updated relative to a preoperative MRI/CT.

14 Claims, 7 Drawing Sheets

(51) Int. Cl.
*A61B 8/12* (2006.01)
*A61B 17/00* (2006.01)
*A61B 17/34* (2006.01)
*A61B 34/30* (2016.01)
*A61B 34/10* (2016.01)
*A61B 90/00* (2016.01)

(52) U.S. Cl.
CPC .......... *A61B 17/3423* (2013.01); *A61B 34/76* (2016.02); *A61B 34/30* (2016.02); *A61B 2017/00398* (2013.01); *A61B 2017/3445* (2013.01); *A61B 2034/107* (2016.02); *A61B 2034/2055* (2016.02); *A61B 2034/2063* (2016.02); *A61B 2034/2068* (2016.02); *A61B 2034/2072* (2016.02); *A61B 2034/302* (2016.02); *A61B 2090/3983* (2016.02)

(58) Field of Classification Search
CPC .... A61B 2034/2072; A61B 2090/3983; A61B 2034/302; A61B 2034/107; A61B 2034/108; A61B 17/00234; A61B 17/3423; A61B 2017/00398; A61B 2017/3445
See application file for complete search history.

(56) References Cited

U.S. PATENT DOCUMENTS

| | | |
|---|---|---|
| 2007/0287992 A1 | 12/2007 | Diolaiti et al. |
| 2008/0200927 A1* | 8/2008 | Hartmann ............ A61B 90/36 606/130 |
| 2012/0226145 A1 | 9/2012 | Chang et al. |
| 2014/0276937 A1 | 9/2014 | Wong et al. |

FOREIGN PATENT DOCUMENTS

| | | |
|---|---|---|
| CN | 103281968 A | 9/2013 |
| DE | 102010029275 A1 | 12/2011 |
| WO | 1998038908 A1 | 9/1998 |
| WO | 2013080070 A1 | 6/2013 |

OTHER PUBLICATIONS

International Search Report for PCT/US2014/060066, dated Jan. 14, 2015.

International Preliminary Report on Patentability for PCT/US2014/060066, dated Nov. 24, 2015.

Office Action received in corresponding Chinese Application No. 201480067377.7 dated Feb. 23, 2018.

* cited by examiner

SYSTEM FOR AND METHOD OF PERFORMING SONASURGERY

CROSS-REFERENCE TO RELATED APPLICATION

This application is the United States national stage application of International Application No. PCT/US2014/060066, filed Oct. 10, 2014, which claims benefit of U.S. Provisional Application No. 61/889,863, filed Oct. 11, 2013, both of which are herein incorporated by reference in their entirety.

SUMMARY

The field of general surgery and specifically abdominal surgery has experienced technology advances over the past 50 years, but overall has arguably experienced little change in general surgical practice. First there was open surgery—a single big incision with large instruments in a large open space. Then the field moved into the realm of laparoscopic surgery—multiple smaller incisions with reduced size instruments passed through the incisions. This was followed by robotic surgery—even smaller multiple openings plugged with ports through which small customized tools held in place by an external motorized device are passed, whereby the surgeon, sitting remote to the patient, is able to guide the procedure with the external motors mimicking his movements. Most recently single port surgery has been introduced to the field, whereby the surgeon uses a single port that has multiple small passages in it for multiple tools.

Regardless of technology, current surgery methods still focus on the same procedures, with the same surgical issues and, perhaps most importantly, the same outcomes. With each of the known approaches, the surgeon typically must probe, spread, cut, buzz, and suck tissue, using direct visualization or fiber optic imaging technology introduced through an additional port, to see where he or she is. A knife is used to remove the tissue targeted for destruction, requiring room within the surgical field to maneuver. The use of a knife creates bleeding that creates an even greater need for room in order to control the bleeding. The surgeon often uses preoperative ("preop") surgical images to guide her mental view of the world but not to guide actual the procedure as is done in radiation therapy (RT) or stereotactic neurosurgery. In general surgery, there is no link or connection made between the preoperative data derived from images and the operative visual data. The surgeon often needs an assistant to help hold tools just like with open surgery, optically imaging in order to see where she is inside the patient, and often needs to trust her ability to relate the small window of visualization achieved through the optical scope with the entire extent of the patient. While she can create a plan for the surgical procedure using computers, the execution of that plan is completely under the direction and control of the surgeon, the entire procedure is typically performed based on manual movement and a "one step at a time" attitude. Even with "robotic surgery," there is typically no robot in the classical sense of an automaton that makes decisions or even just moves on its own. Instead, the "robot" is a "waldo," where the movement of the "robotic" instruments mirror the movements of the surgeon who is displaced geographically from the actual operative field.

A feature common to all laparoscopic and robotic procedures is the use of carbon dioxide ($CO_2$) gas to insufflate the body cavity in order to create enough room for the surgeon to manipulate the instruments required to perform the desired procedure. The working space developed by $CO_2$ (pneumoperitoneum or pneumoretroperitoneum) depends on the pressure of gas presented to the patient; the higher $CO_2$ insufflation pressure the better view of the surgical field but the greater the risk of complications.

The physiologic effects seen with $CO_2$ insufflation may be transient and derive from the body's reaction to increases in intra-abdominal pressure, compromises in respiratory function resulting from increased abdominal pressure, and changes in body chemistry secondary to $CO_2$ absorption. People who are otherwise healthy will tolerate laparoscopy well, while individuals with underlying cardiopulmonary or renal diseases may not tolerate prolonged $CO_2$ insufflation. Additionally, patient positioning, for example the steep trendelenburg used in prostatectomy, can exacerbate cardiovascular alterations in laparoscopy. Regardless, the need to provide insufflation requires additional equipment, cost, and potential complications that can be life threatening in compromised patients.

It can be seen that each sequential advancement in surgical approach—from open surgery to laparoscopy to robotics to "single" port—can be viewed as open surgery modified by the number and size of the surgical openings and instruments employed and by the "location" of the surgeon's hands; from the surgeon's hands being inside the patient, to outside but adjacent to the patient, to remote to the patient. However, effectively these same hands handle a surgical blade that is used to out tissue, creating the bleeding that these same or other hands must then stop.

Therefore, what is desirable is a new approach to the surgical elimination of targeted tissue, one that generally, if not completely, obviates the need for the knife and its associated bleeding, one that allows procedures to be done using a single port, one that provides a way to relate intraoperative data with preoperative data, and/or one that allows the procedure to proceed as planned under the direction of the surgeon but executed by the computer or robot.

In one embodiment, the present disclosure includes a series of interchangeable surgical probes. Each probe may be designed for a specific purpose, such as dissecting, probing, spreading, sucking, biopsing, and altering tissue, all to be introduced through a common sheath, with each probe including some combination of at least two technologies from a list including, but not limited to, optical imaging, diagnostic imaging, ultrasound imaging, tissue alteration, tactile feedback, and positional verification/tracking, thereby providing the capability for generating transient or permanent change within tissue while verifying position and the clinical state of the tissue being changed and/or the status of surrounding tissue. Each of the probes may vary in size (e.g., length, diameter, etc.). The technologies or tools may be installed at the distal end of a rigid or flexible or articulating shaft whose proximal end may be connected to an integral set of motors or to a remote set of motors, activated manually or under computer control, to adjust the position and/or orientation of the distal end of the shaft distinct from the position and/or orientation of the shaft itself. These motors can control all or some combination of: bending of the proximal and distal shafts, rotation of the proximal and distal shafts, and lengthening of the distal end of the shaft.

Probes with optical imaging capabilities can be used to determine where the probe is in the tissue, may include, but are not limited to, a light pipe and a lens for viewing. Probes with diagnostic imaging capabilities may include, but are not limited to, gamma technology, near infrared light technology, and interrogative ultrasound (US) technology. Probes with ultrasound imaging capabilities for assessing the internal aspects of the target and surrounding tissue may include, but are not limited to, an imaging transducer of variable frequency of any design including 2-D, 3-D scanning, annular, linear, and phased array. Probes with tissue altering technology (either permanently or reversibly) may include, but are not limited to, any form of technology used to produce alteration of tissue by thermal or electrical or other means such as laser, RF, microwave, cryo, US, IRC. Probes with tactile feedback may include, but are not limited to, haptic feedback systems and pressure sensors. Probes with positional verification technology, used to track where the instrument is in space relative to a known reference point, may include, but are not limited to, any form of technology used to identify and/or track the position of an object in three dimensional space relative to a known point, such as optical, electromagnetic, and RF.

Computer or manual controlled movement of the various degrees of freedom of the system allows adjustment of the shape and position of a sheath and any probe introduced through the sheath, whereby the probe can be inserted through a single small opening in the patient, with the distal end of the probe delivered to the target tissue along a path and in a manor determined by a treatment planning system, in order to image, assess, and potentially alter, tissue.

In a further embodiment of the present disclosure, a targeting device with at least two degrees of freedom may be mounted over a created or natural opening in a patient, whereby the sheath and probes may be introduced through the sheath and at least partially into a patient. This may be done in a direction and/or along a trajectory consistent with the determined by a treatment planning system.

In another embodiment of the present disclosure, a system and method for delivering a surgical treatment includes performing preoperative imaging and treatment planning to identify a target volume to treat and an optimal path to the target volume based on the known tissue altering characteristics of a probe. An optimal port placement for probe introduction may be determined in order to reach the target volume. A noninvasive form of imaging, such as US, localized to a known fixed landmark that establishes the room coordinate system, may be used to image the region of the target volume at the time of therapeutic intervention. Operative images may be fused to the preop images, thereby registering the target, as seen in the preop images, to a room coordinate system. Existing or mounted landmarks on patient surface may be identified using a localization technology, such as electromagnetic or optical tracking systems. A single port may be placed at the predetermined location by transferring its position on the preop images as determined by the treatment planning system to the patient relative to the room coordinate system. A sheath, with an internal obturator that includes a light pipe, may be introduced through the port in the orientation determined by treatment plan and established by the localization/tracking device. One or a range of interchangeable probes may be introduced or inserted through the sheath to allow point of treatment to be reached with all probes and tools including. All work done may be accomplished using fiber optic visualization incorporated into the probe (with or without US) with position of probe tracked in real time and displayed on a treatment screen through the incorporation of localization technology into the probe. The sheath may be advanced as and if needed in order to deliver the probes to the correct location as the procedure proceeds. A probe may be introduced to the target volume that includes tissue altering capability among its incorporated technologies, thereby allowing tissue to be accessed and altered through a single port without bleeding and without the need for additional ports and instrumentation.

The present disclosure also includes a system and method for delivering a surgical treatment including performing preoperative imaging and treatment planning to identify a target volume to treat and an optimal path to the target volume based on the known tissue altering characteristics of the probe. An optimal port placement for probe introduction may be determined in order to reach the target volume. A noninvasive form of imaging, such as US, localized to a known fixed landmark that establishes the room coordinate system, may be employed to image the region of the target volume at the time of therapeutic intervention. Operative images may be fused to the preop images, thereby registering the target, as seen in the preop images, to a room coordinate system. Existing or mounted landmarks may be identified on a patient surface using a localization technology such as electromagnetic or optical tracking systems. A single port may be placed at the predetermined location by transferring its position on the preop images as determined by the treatment planning system to the patient relative to the room coordinate system. A motorized targeting system may he mounted over the port and the orientation of the targeting system may be adjusted along a predetermined and computer controlled trajectory. A sheath, with an internal obturator that includes alight pipe, may be inserted or introduced through the targeting system and then the port. One or a range of interchangeable probes may be inserted or introduced through the sheath to allow point of treatment to be reached with all probes and tools including, and all work done under, fiber optic visualization incorporated into the probe (with or without US) with position of tool tracked in real time and displayed on the treatment screen through the incorporation of localization technology into the probe. The sheath may be advanced as and if needed in order to deliver the probes to the correct location as the procedure proceeds. A probe may be introduced to the target volume that includes tissue altering capability among its incorporated technologies, thereby allowing tissue to be accessed and altered through a single port without bleeding and without the need for additional ports and instrumentation.

Another system and method for delivering a surgical treatment according to an embodiment of the present disclosure includes performing preoperative imaging and treatment planning to identify a target volume to treat and an optimal path to the target volume based on the known tissue altering characteristics of the probe. An optimal port placement for probe introduction may be determined in order to reach the target volume, A noninvasive form of imaging, such as US, localized to a known fixed landmark that establishes the room coordinate system, may be used to image the region of the target volume at the time of therapeutic intervention. Operative images may be fused to the preop images, thereby registering the target, as seen in the preop images, to a room coordinate system. Existing or mounted landmarks may be identified on a patient surface using a localization technology such as electromagnetic or optical tracking systems. A single port may be placed at the predetermined location by transferring its position on the preop images as determined by the treatment planning system to the patient relative to the room coordinate system. A sheath, with an internal obturator that includes a light pipe, may be inserted or introduced through the targeting system and then the port. One or a range of interchangeable probes may be inserted or introduced through the sheath to allow point of treatment to be reached with all probes and tools including, and all work is done under, fiber optic visualization incorporated into the probe (with or without US) with position of tool tracked in real time and displayed on the treatment screen through the incorporation of localization technology into the probe. The orientation of various portions of the probe may be modified relative to the surrounding tissue and to itself under computer control. The sheath may be advanced as and if needed in order to deliver the probes to the correct location as the procedure proceeds. A probe may be introduced to the target volume that includes tissue altering capability among its incorporated technologies, thereby allowing tissue to be accessed and altered through a single port without bleeding and without the need for additional ports and instrumentation.

According to another embodiment of the present disclosure, a system and method of delivering a surgical treatment includes performing preoperative imaging and treatment planning to identify a target volume to treat and an optimal path to the target volume based on the known tissue altering characteristics of the probe. An optimal port placement for probe introduction may be determined in order to reach the target volume. A noninvasive form of imaging, such as US, localized to a known fixed landmark that establishes the room coordinate system, may be used to image the region of the target volume at the time of therapeutic intervention. Operative images may be fused to the preop images thereby registering the target, as seen in the preop images, to a room coordinate system. Existing or mounted landmarks may be identified on a patient surface using a localization technology, such as electromagnetic or optical tracking systems. A single port may be placed at the predetermined location by transferring its position on the preop images as determined by the treatment planning system to the patient relative to the room coordinate system. A motorized targeting system may be placed on or over the port and the orientation of the targeting system is adjusted to correspond to a predetermined and computer controlled trajectory. A sheath, with an internal obturator that includes a light pipe, may be introduced through the targeting system and then the port. One or a range of interchangeable probes may be introduced through the sheath to allow point of treatment to be reached with all probes and tools including, and all work is done under fiber optic visualization incorporated into the probe (with or without US) with position of tool tracked in real time and displayed on the treatment screen through the incorporation of localization technology into the probe. The orientation of various portions of the probe may be modified relative to the surrounding tissue and to itself under computer control. The sheath may be modified as and if needed in order to deliver the probes to the correct location as the procedure proceeds. A probe may be introduced to the target volume that includes tissue altering capability among its incorporated technologies, thereby allowing tissue to be accessed and altered through a single port without bleeding and without the need for additional ports and instrumentation.

As is to be appreciated by one skilled in the art, one or more aspects of the foregoing disclosed systems and methods may be combined or even omitted, if desirable.

DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown.

FIGS. 3(a)-(d) are elevational views of various components according to embodiments of the present disclosure.

Figure 4A:
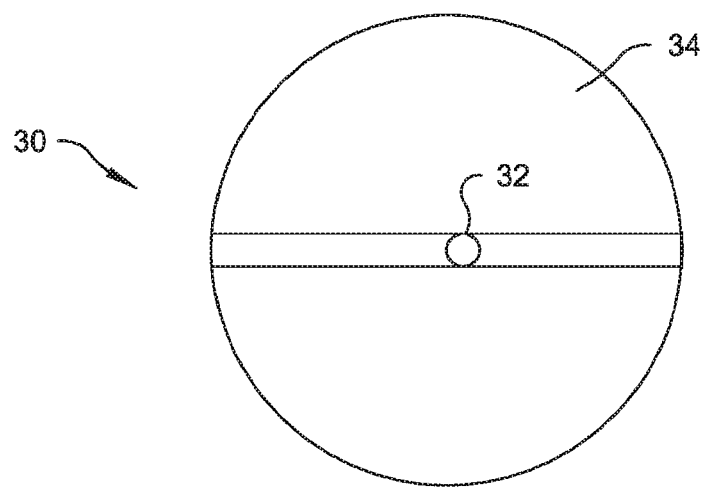
Figure 4B:
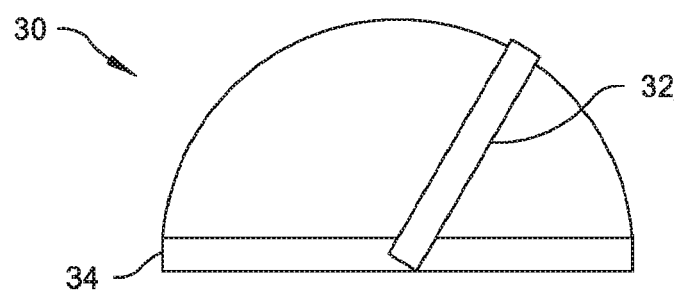

FIGS. 4A-B are top plan and an elevational views, respectively, of a targeting device according to an embodiment of the present disclosure.

Figure 4C:
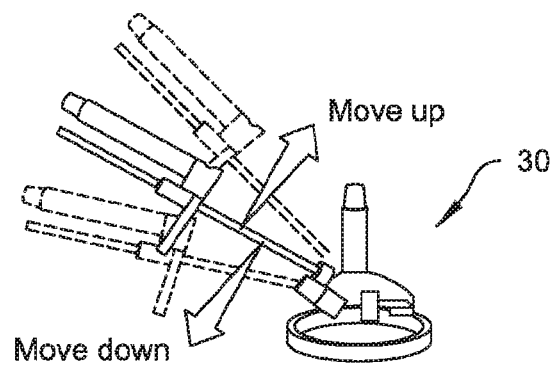
Figure 4D:
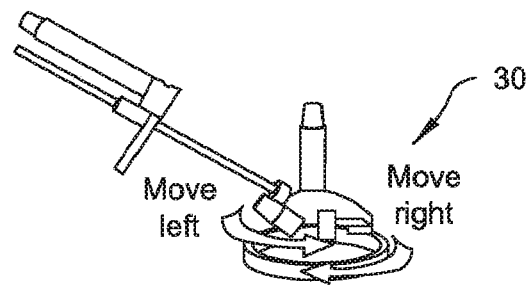
Figure 4E:
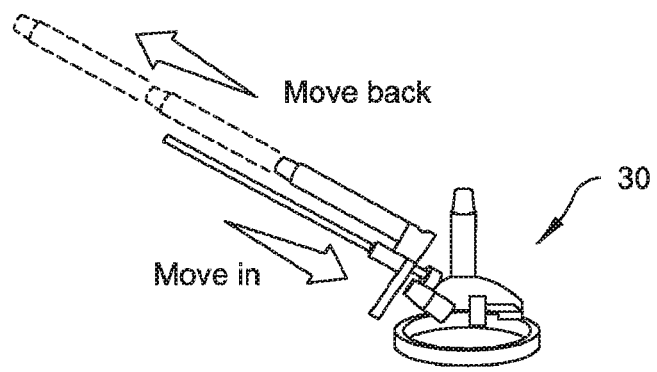

FIGS. 4C-E are perspective views of a targeting device according to another embodiment of the present disclosure, wherein the targeting device is shown in various configurations.

Figure 5:
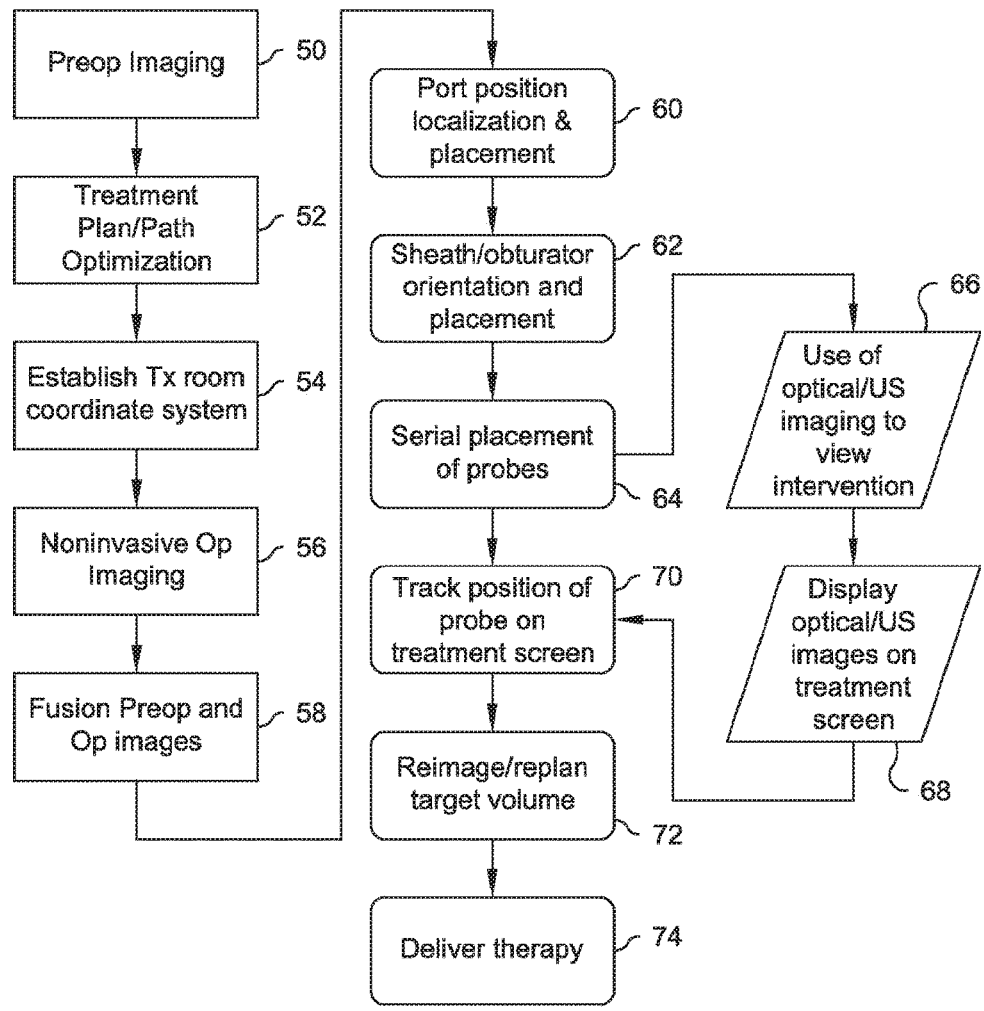

FIG. 5 is a flow diagram according to an embodiment of the present disclosure.

Figure 6:
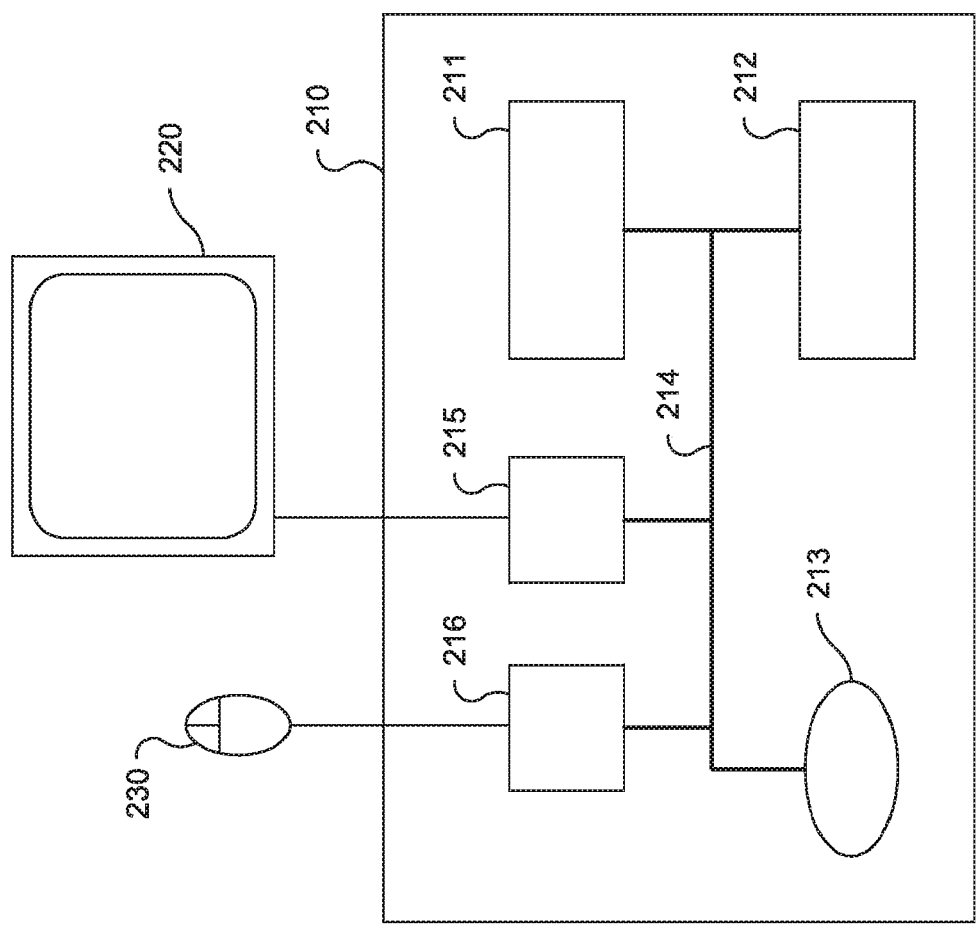

FIG. 6 is a schematic diagram of an exemplary computing device useful for performing at least certain processes disclosed herein.

DETAILED DESCRIPTION

Various embodiments of the present disclosure are described hereinafter with reference to the figures. It should be noted that the figures are not drawn to scale and elements of similar structures or functions are represented by like reference numerals throughout the figures. It should also be noted that the figures are not intended to facilitate the description of specific embodiments of the invention. The figures are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. It will be appreciated that while various embodiments of the invention are described in connection with radiation treatment of tumors, the claimed invention has application in other industries and to targets other than cancers. Unless specifically set forth herein, the terms "a," "an" and "the" are not limited to one element, but instead should be read as "at least one."

The present disclosure includes a system for performing a surgical procedure, the system including at least one sensor configured to provide at least one image of a target volume of a patient using noninvasive technology. A coordinate system is established in a treatment room containing the patient. A single surgical port is created in the patient proximate to the target volume, At least one probe is configured to be inserted at least partially into the single surgical port. The probe includes a shaft and at least one tool at a distal end thereof. The proximal end of the shaft may be operatively connected to at least one motor to permit manipulation of at least one of a position and an orientation of the tool. At least one controller may be configured to i) integrate the at least one image from the sensor with the coordinate system, ii) identify a location on the patient to create the single surgical port to provide access the target area, iii) manipulate at least a portion of the probe to treat the target area, iv) track the tool in real-time, and/or v) display the position of the tool on a screen.

The present disclosure also includes a method of performing a surgical procedure that may involve taking, receiving or obtaining preoperative images of at least a portion of a patient, receiving a treatment plan that identifies an optimal path to a target volume of the patient, determining an optimal placement for insertion of a probe into the patient to reach the target volume. Existing or mounted landmarks may be identified on the patient, and a single port is created at a predetermined location in the patent. A sheath may be inserted at least partially into the patient, and at least one probe is inserted at least partially into the sheath. At least a portion of the probe includes localization technology. At least a portion of the target volume is treated utilizing at least one tool of the probe.

More particularly, in one embodiment as depicted in FIGS. 1(a)-1(g), at least one or a series of surgical probes 10 may be provided based on a common platform, one that includes a range of technologies that provide imaging, diagnosis, localization, and/or tissue altering capabilities. In at least one embodiment, each probe 10 includes a shaft 12 that may be at least partially or completely rigid (see FIG. 3A), at least partially or completely articulated (see FIG. 3B), and/or at least partially flexible (e.g., due to a flexible and/or resilient material or one or more linkages). At leak two and possibly four or more of the technologies may be deployed or utilized at the distal end of the shaft 12.

The shaft 12 or at least a portion thereof may be manipulated by manual and/or computer control. The proximal end of each shaft 12 may be sized, shaped and/or configured to mate with at least one or a set of motors 14 designed to effect the position and orientation of the proximal and/or distal ends of the shaft 12, The motors 14 may be integral to the shaft 12 (see FIGS. 1(a)-1(g) and 3A), or the set of motors 14 may be external to and connected directly to the shaft 12 (see FIG. 3C) or to a mechanism that itself contains motors 14, such as a surgical robot 16 (see FIG. 3D). In one embodiment, the motors 14 may be used to control independently the position and/or orientation of at least the distal end of the shaft 12 relative to the position and/or orientation of the proximal end of the shaft 12, including all or some combination of: bending of the proximal and distal shafts 12, rotation of the proximal and distal shafts, linear translation of the distal and proximal shafts 12.

Figure 2:
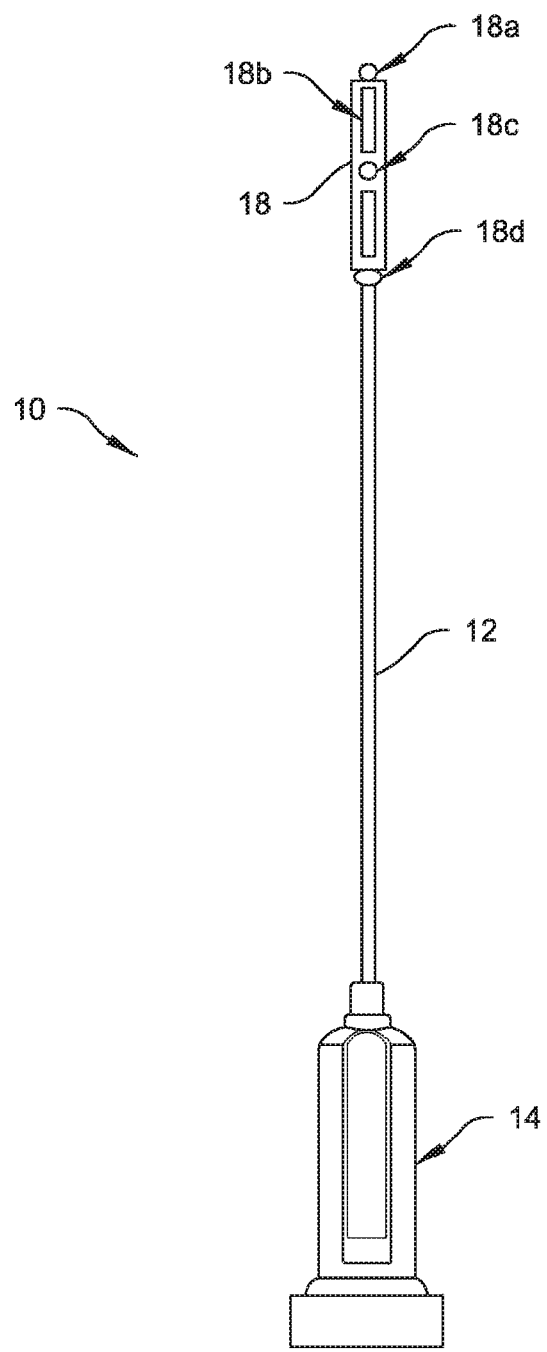
FIG. 2 is an enlarged elevational view of the probe shown in FIG. 1(g)
Figure 3A:
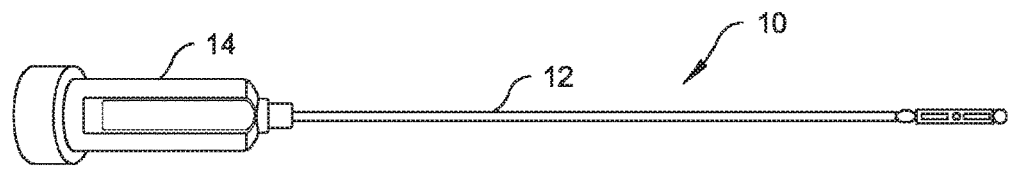
Figure 3B:
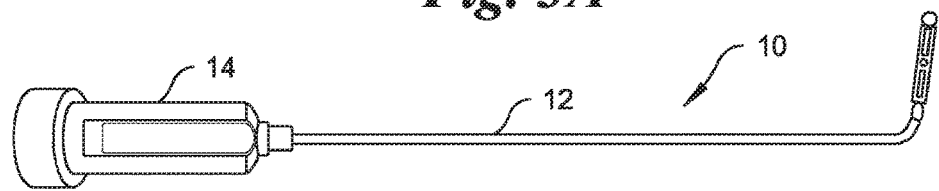
Figure 3C:
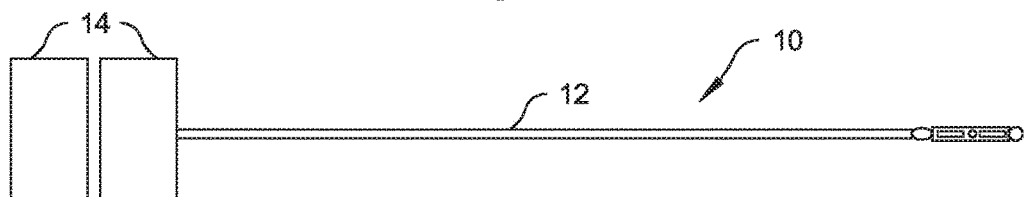
Figure 3D:
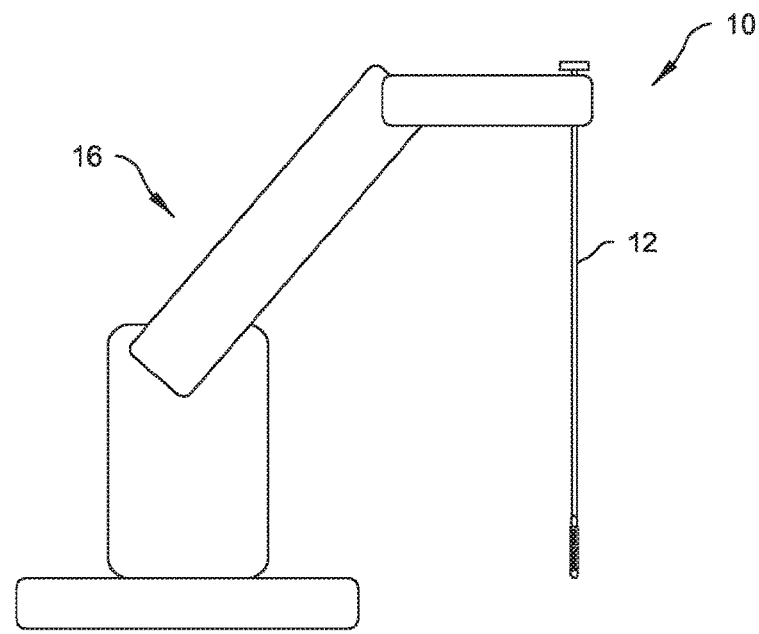

In an embodiment, a tool 18 at the distal end of each probe 10 is designed to perform at least one distinct function (see FIGS. 1(b)-1(g)) including, but not limited to, tissue dissection, tissue spreading, tissue sampling, fluid aspiration, tissue aspiration, and tissue irrigation. In addition, each probe 10 may include the aforementioned at least two technologies devoted to imaging, diagnosis, localization, and tissue alteration (see FIG. 2). For example, as shown in FIG. 2, the tool may include localization 18a, therapy 18b, US imaging 18c and/or optical imaging light source 18d technologies. Intra-tissue US and fiber optics may be incorporated into each probe 10. The US permits visualization of the interior of the target area, while the fiber optics permit visualization exterior of the target area.

Imaging includes any means designed to provide images of the surface or interior of tissue. Technologies designed to provide images of the surface of tissue include, but are not limited to, the optics required to view any wavelength such as the visual spectrum or the near-infrared spectrum or the ultraviolet spectrum and include means for the transmitting of light to the tissue and means for sending images of the tissue back to the user.

Technologies designed to provide diagnostic interrogation of tissue include, but are not limited, to gamma imaging, near infrared light imaging, x-rays, and nuclear magnetic resonance. Technologies designed to provide images of the interior of the tissue include, but are not limited to, diagnostic ultrasound, various penetrating optical frequencies such as near-infrared and ultraviolet imaging, gamma camera, and nuclear magnetic resonance. US technology includes transducers of variable frequency of any design including, but not limited to, 2-D, 3-D scanning, annular, linear, and phased arrays.

Technologies designed to provide tissue alteration, used to permanently or reversibly alter the function of tissue or to destroy tissue, may include any form of technology used to alter tissue by thermal, electrical or other means such as laser, radio frequency (RF), microwave, cryo, US, irreversible electrocorpation (IRC). Tissue altering technologies may be used for permanent disruption of cellular function and/or anatomy or for transient disruption of cellular function and/or anatomy. An example of reversible alteration of tissue function is the use of focused ultrasound at low intensity to effect or improve tissue membrane permeability such that cancer destroying drugs can better enter cells. An example of permanent alteration of tissue is the use of high intensity focused ultrasound to destroy cancer cells through thermal ablation.

The one or more probes 10 with positional verification technology, used to track where the respective probe 10 is in space relative to a known reference point, may include any form of technology used to identify and/or track the position of an object in a three dimensional space relative to a known point such as optical, electromagnetic, and radiofrequency.

Figure 1A:
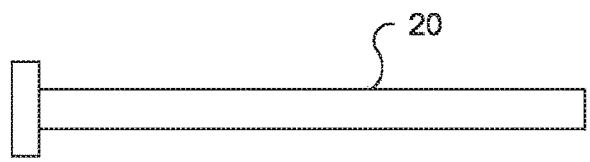
FIG. 1(a) is an elevational view of a sheath according to an embodiment of the present disclosure.
Figure 1B:
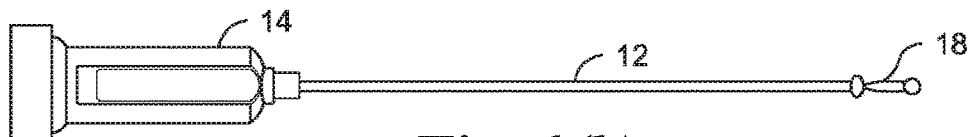
FIG. 1(b) is an elevational view of a probe according to an embodiment of the present disclosure, wherein a distal end of the probe includes imaging and localization technologies.
Figure 1C:
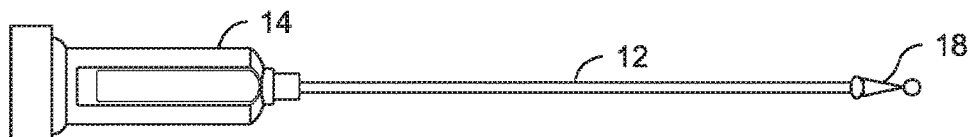
FIG. 1(c) is an elevational view of a probe according to an embodiment of the present disclosure, wherein a distal end of the probe includes optical and localization technologies.
Figure 1D:
FIG. 1(d) is an elevational view of a probe according to an embodiment of the present disclosure, wherein a distal end of the probe includes Ultrasound localization technology.
Figure 1E:
FIG. 1(e) is an elevational view of a probe according to an embodiment of the present disclosure, wherein a distal end of the probe includes a tissue spreader with optical technology.
Figure 1F:
FIG. 1(f) is an elevational view of a probe according to an embodiment of the present disclosure, wherein a distal end of the probe includes biopsy and optical technologies.
Figure 1G:
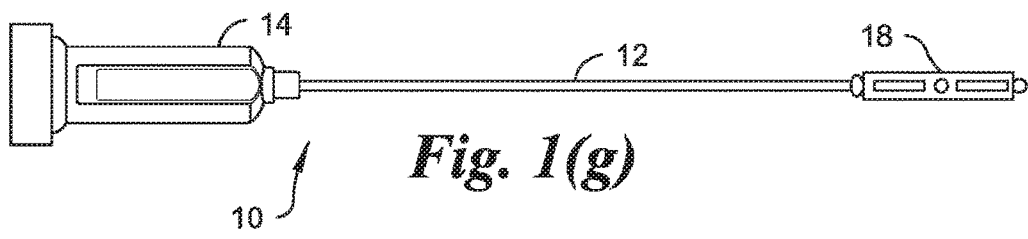
FIG. 1(g) is an elevational view of a probe according to an embodiment of the present disclosure, wherein a distal end of the probe includes high intensity focused ultrasound with optical technology, as well as Ultrasound imaging and localization technologies.

As shown in FIG. 1(a), a single sheath 20 may be introduced at least partially into a patient through a single surgical port through which all of the probes 10 can pass. In contrast to many conventional surgical procedures, the procedure of the present embodiment is able to complete the surgery with only a single surgical port. The sheath 20 may include an obturator (see, for example, FIG. 1(b)) that fits at least partially or even completely inside the sheath 20. The obturator being a variant on the probes 10 described above. That is, the obturator 10 may include at least two of the technologies, including at least one from either tissue surface or tissue interior imaging as well as a localization/tracking technology. By positioning and orienting the sheath 20 as dictated by the treatment planning system (described in detail below), the probes 10 can be at least partially or even completely introduced or inserted into and removed from the sheath 20 interchangeably while maintaining orientation of all of the probes 10 along the same or substantially the same trajectory.

The above-described embodiment of the present disclosure is distinct from conventional single port surgical procedures because these prior art procedures enlarge the size of the port to allow multiple tools to be inserted at one time or in parallel. An embodiment of the present disclosure permits a smaller port to be utilized during the surgical procedure. As a result, the present embodiment reduces the cutting, tearing, bleeding, etc. that results from surgical procedures and results in less trauma to the patient and quicker recovery times.

In order to orient the sheath 20 and/or the probes 10 correctly within the surgical port, at least one embodiment of the present disclosure employs a targeting device or system 30 (see FIGS. 4A-4E). FIG. 4A is a top plan view of the targeting device 30. FIG. 4B is a side elevation view of the targeting device 30 with at least a portion of the targeting device 30 in an alternate position. FIGS. 4C-4E are perspective views of the targeting device 30 that show various movement of the probe 10 that the targeting device 30 permits. In at least one embodiment, the targeting device 30 may permit and/or enable a wide range of motion (e.g., upward, downward, left, right, inward, outward or any combination thereof) of the sheath 20 and/or the probes 20 with respect to the patient. The targeting device 30 may be of any form that allows a trajectory to be established either manually or under computer control through the incorporation of motors or other forms of drive system. For example, the targeting device 30 may have a structure similar to those used in the field of neurosurgery and orthopedics to aim a probe or other surgical instrument in a desired direction.

The targeting device 30 may include a means for fixating a base or plate 34 of the targeting device 30 in position relative to the patient, either by securing it directly or indirectly to the patient, to the table on which the patient may lie, to a support structure deployed adjacent to the table, and/or to the room itself. The targeting device 30 may include a means for passing the sheath 20 and/or the probe 10 at least partially or even completely through the targeting device 30 along the trajectory established by the targeting device 30. The means for passing may be a tube 32 with a circular cross-sectional shape. The cross-sectional area and/or shape of the tube 32 may be only slightly larger than that of each probe 10, such that only one probe 10 may be inserted into the tube 32 at a time. The targeting device 30 also may incorporate localization technology in order to identify the proper orientation of the targeting aspect of the device.

Computer or manual controlled movement of the various degrees of freedom of the targeting device 30, and of the shaft 12 of a given probe 10 once introduced into the targeting device 30, allow adjustment of the shape and/or position of the probe 10 introduced through the single, small opening in the patient, with the distal end of the probe delivered to the target tissue along a path and in a manor determined by a treatment planning system, in order to image, diagnose, and/or potentially alter tissue.

In an embodiment, as shown in FIG. 5, preoperative imaging of the region of the patient in question may be performed, received and/or obtained with data downloaded into a treatment planning system, such as a computer and a sensor, used to identify a target volume (e.g., size, shape and/or location) of a portion of the patient (e.g., the prostate or a portion thereof) to alter or remove during surgery (Step 50). Imaging may also be performed prior to creation of the single, small opening into the patient to determine an optimal path to reach the target volume within the patient with at least a portion of the probe 10 based on the known tissue altering characteristics of the technology to be used to alter the region in question. In one embodiment, the imaging may be accomplished by placing a sensor on or near a portion of the patient. The position of the sensor may be manipulated manually or through computer control. The sensor may be spaced-apart from but operatively connected to the computer. Part of the treatment planning process may include determining an optimal location for port placement for the probe 10 introduction into the patient in order to reach the target volume (e.g., the spleen or a portion thereof) while minimizing complications to the patient (Step 52). Once the optimal location is determined, its coordinates may be saved in the treatment planning system.

At the time of treatment, a coordinate system may be established in the treatment room using a localization technology (Step 54). The coordinate system may be a means for creating a uniform reference point used in the operating room, radiation oncology suite, and/or on the images. A coordinate system can be established in any number of ways known to those skilled in the art. For instance, a minimum of three reference markers may be placed on the patient surface (e.g., skin) prior to imaging, the locations of which are marked by tattoos. The reference markers can be identified on the preoperative images with the location of a point on the images referenced to the markers. At the time of treatment the localization probe can be used to identify the position of the minimum of three points in order to reestablish the reference system used at the time of imaging. Alternatively, natural occurring points on the patient surface can be used, for instance, the umbilicus. In addition, registration can occur without any points. At the time of treatment, the probe 10 with localization can be traced over the patient surface with the computer recording continuously the probe 10 position until such time as the computer system has captured enough points to generate a contour of the patient that can be fused with the contour of the patient generated from the imaging data.

The coordinate system may be affixed to a noninvasive form of imaging, such as US, which is used to image the region of the target volume (Step 56). Alternatively, a system such as a magnetic resonance imaging (MRI) with its own inherent coordinate system may be used for imaging. The images generated in the treatment room may be fused to or combined with the preoperative images by a computer or controller, for example, thereby registering the location of the target volume, as determined in the preoperative images, to a room coordinate system existent at the time of treatment (Step 58). The fusion can be accomplished by one or more of any number of approaches known to those skilled in the art, such as deformable registration, fixed registration, etc. Using a pointer equipped with localization technology, for example, the location for the entrance of probes into the patient on the patient surface can be identified.

After the size, shape and location of the target volume is identified and/or after the path to reach the target volume is identified, a small, single surgical port can be placed or created in the patient (Step 60). The surgeon may make the incision by hand. The sheath 20, with an internal obturator that includes a light pipe and localization technology, for example, can be introduced at least partially or even completely through the single port (Step 62). By equipping the obturator 10 with localization technology, the sheath 20 can be oriented consistent with the orientation determined by treatment planning system. In other words, once the desired path to the target volume is established and/or precisely mapped prior to surgery, the path can be implemented or followed during surgery because the position and/or location of at least the distal end of the probe 10 is known and can be seen optically and/or with US. During surgery, the present disclosure permits the surgeon or operator to manipulate a computer keyboard, a touch screen and/or a computer mouse, for example, to perform the surgery.

In other words, in at least one embodiment, the system may determine the location of optimal port placement. The localization technology may be used to locate this point on the patient. particular, a probe 10 with localization may he moved around on a surface of the patient until the system identifies it as corresponding to the point determined by the computer to be optimal given the location of the target and any obstacles that may exist in its path. The surgeon then may make an incision at that point.

A range of probes 10, each performing a specific function, and each equipped with at least two technologies from a list including imaging, diagnosis, localization, tactile feedback, and/or tissue altering capabilities, may be introduced or inserted interchangeably or in series through the sheath 20, thereby allowing each probe 10 to be directed toward the treatment volume (Step 64). The position of the probes 10 can be tracked in real-time and displayed on a treatment planning screen, such as a computer monitor, due the incorporation of localization technology into each probe 10. The optical and US images generated by probes 10 that are so equipped can be displayed as well on the treatment planning screen (Steps 66 and 68). Once the target volume of the patient has been reached by at least a portion of the probe 10 and the region prepared using probes 10 designed to do so (Step 70), imaging of the treatment volume can be repeated using a suitably equipped probe 10 (Step 72), the treatment plan updated based on existing anatomy, and a tissue altering probe 10 delivered to the target volume that includes permanent or reversible tissue altering capability among its incorporated technologies, thereby allowing tissue to be accessed and altered through the small, single port under optical and/or US imaging without bleeding and without the need for additional ports and instrumentation (Step 74).

In a further embodiment of the present disclosure, a manual or motorized targeting system 30 may be mounted at least partially or completely over the port formed in the patient and may be used to adjust and/or maintain the orientation of the sheath 20 and/or the probes 10 along a predetermined and, in the case of the motorized system, computer controlled trajectory. For example, when employing a probe 10 with an articulated or bendable shaft 12, the computer, by knowing the position of at least a portion of the distal end of the probe 10 through the on-board localization system, can adjust the position of each aspect of the probe 10 in order to bring at least a portion of the distal end of the probe 10 to a desired location within or near the patient. A feedback loop may be established that recognizes that at least a portion of the distal end of the probe 10 has moved, records and/or stores the new position, and determines where to move at least a portion of the distal end of the probe 10 to position the probe 10 in the desired position or a position necessary to perform a surgical procedure. Thus, the position of each surgical tool can be tracked continuously during the course of the procedure so that its position is known and updated relative to the preoperative MRI/CT.

In a means of operation according to a further embodiment of the present disclosure, the orientation of various portions of each probe 10 relative to the surrounding tissue and to itself can be modified under computer control in order to change the shape of at least a portion of the probe 10 in order to reach a greater range of locations such as around corners.

A major benefit of the technique described herein is the reduction in use of or even the elimination of the surgical knife. In current surgical practice, the need to wield a knife generally necessitates extensive exposure of the region to be treated which generally requires the use of insufflation techniques to create such space in closed anatomical compartments. Bleeding is a common result of the use of a knife which in turn often requires even further exposure to control as well as the use of additional instruments employed by additional surgeons through additional ports placed in the patient. In generally, all of these interventions must be done under optical viewing which requires the placement of an additional port for the light source and fiber optic camera used to visualize the region.

When a knife is not used to eliminate target tissue, the major reason for extensive surgical exposure and the major cause of bleeding are generally eliminated, thereby reducing the need for more than one instrument at a time, thus the number of ports, and in sum the time it takes to perform a procedure. When the path to the target is determined prior to surgery, the path can be optimized to minimize the side effects resulting from intervention. When the position of each surgical tool is tracked during the course of the procedure, the status of the procedure relative to the predetermined optimized path can be assessed and corrections made where required.

One or more of the above-described techniques and/or embodiments may be implemented with or involve software, for example modules executed on or more computing devices 210 (see FIG. 6). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power. The storage device(s) 213 may be any type of non-transitory storage device (e.g., an optical storage device, a magnetic storage device, a solid state storage device, etc. The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the display device 220 (e.g., in response to modules executed). The input controller(s) 216 may be operatively coupled (e.g., via a wired or wireless connection) to an input device 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 6 illustrates the computing device 210 output device 220, and the input device 230 as separate devices for ease of identification only. However, the computing device 210, the display device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud services running on remote computing devices.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A system for performing a surgical procedure, the system comprising:
preoperative images of a region of a patient to be treated;
a room coordinate system established by a minimum of three reference markers placed or identified on the patient, the room coordinate system configured to create a uniform reference point in an operating room for the surgical procedure;
a sheath configured to be inserted at least partially into a single surgical port created in the patient proximate a target volume;
a series of interchangeable probes configured to be inserted in series at least partially into the sheath, each probe including a shaft and at least one tool at a distal end thereof, the at least one tool of one of the series of interchangeable probes including i) at least one sensor configured to provide at least one operative image of the target volume of the patient and ii) at least one of a laser, a haptic feedback sensor, a pressure sensor, and a transducer configured to provide at least one of ultrasound imaging and therapy, a proximal end of the shaft of each probe being operatively connected to at least one motor to permit manipulation of at least one of a position and an orientation of the at least one tool; and
at least one controller configured to i) fuse, prior to commencing the surgical procedure, the at least one operative image from the sensor with the preoperative images, ii) manipulate at least a portion of one of the series of interchangeable probes to treat the target volume, iii) track the at least one tool in real-time, and iv) display the position of the at least one tool on a screen,
wherein the at least one controller monitors a position and orientation of the sheath such that the probes are inserted and removed from the sheath while maintaining a desired orientation of all of the probes along a same or substantially same trajectory into and out of the sheath.

2. The system according to claim 1, further comprising:
a targeting system including a base and a tube extending upwardly from a geometric center of the base, the base being stationary with respect to the patient and being mounted over the single surgical port, the tube being pivotable with respect to the base and being configured to receive each of the probes and the sheath therein, wherein each of the probes is inserted into the single surgical port and through the base.

3. The system according to claim 2, the tube is movable toward and away from the base.

4. The system of claim 1, wherein the at least one sensor includes intra-tissue ultrasound to provide visualization of an interior of the target volume, and wherein the at least one sensor includes fiber optics to provide visualization of an exterior of the target volume.

5. The system according to claim 1, further comprising:
a robot containing the at least one motor, the robot connecting the series of interchangeable probes to the at least one motor; and
a targeting system including a base and a tube extending upwardly from a geometric center of the base, the base being stationary with respect to the patient and being mounted over the single surgical port, the tube being pivotable with respect to the base and being configured to receive each of the probes and the sheath therein, wherein each of the probes is inserted into the single surgical port and through the base.

6. A method of performing a surgical procedure, the method comprising:
receiving or obtaining preoperative images of at least a portion of a patient;
receiving a treatment plan that identifies an optimal path to a target volume of the patient;
determining an optimal placement for insertion of a probe into the patient to reach the target volume;
identifying existing or mounted landmarks on the patient;
creating a single port at a predetermined location in the patient;
placing a targeting system at least partially over the single port, the targeting system including a base and a tube extending upwardly therefrom, the base being placed on top of the patient, the tube being pivotable with respect to the base;

inserting a sheath at least partially into the tube, through the base, and into the single port and into the patient;

inserting a first probe at least partially into the sheath and through the tube and the base, the first probe including at least one of an optical sensor, an electromagnetic sensor, and a radio frequency sensor;

removing the first probe from the sheath, the base, and the tube;

inserting a second probe into the tube, through the base, and into the sheath, the second probe including at least one of a laser, a haptic feedback sensor, a pressure sensor, and a transducer configured to provide at least one of ultrasound imaging and therapy; and treating at least a portion of the target volume by utilizing at least one tool of the second probe.

7. The method according to claim 6, wherein the sheath is introduced into the patient in an orientation determined by the treatment plan.

8. The method according to claim 6, further comprising:
performing a non-invasive form of operative imaging localized to a known fixed landmark that establishes a room coordinate system prior to determining the optimal placement for insertion of the probes into the patient to reach the target volume.

9. The method according to claim 8, further comprising:
fusing operative images with the preoperative images to register the target volume to the room coordinate system.

10. The method according to claim 6, wherein the first probe includes at least one of a light pipe, a lens for viewing, and an image transducer, and wherein one or more images obtained by the first probe are displayed on a treatment screen located exterior of the patient.

11. The method according to claim 10, wherein at least one of a computer keyboard, touch screen and a computer mouse allow a surgeon to manipulate the probes, and wherein the first probe is tracked in real-time through the at least one optical sensor, electromagnetic sensor, and radio frequency sensor.

12. A system for performing a surgical procedure, the system comprising:
a room coordinate system established by a minimum of three reference markers placed or identified on a patient to be treated, the room coordinate system configured to create a uniform reference point in an operating room for the surgical procedure;

a sheath configured to be inserted at least partially into a single surgical port created in the patient proximate a target volume;

a series of interchangeable probes configured to be inserted in series at least partially into the sheath, each probe including a shaft and at least one tool at a distal end thereof, the at least one tool of one of the series of interchangeable probes including i) at least one sensor configured to provide at least one operative image of the target volume of the patient and ii) at least one of a laser, a haptic feedback sensor, a pressure sensor, a transducer configured to provide at least one of ultrasound imaging and therapy, an optical sensor, an electromagnetic sensor, and a radio frequency sensor, a proximal end of the shaft of each probe being operatively connected to at least one motor to permit manipulation of at least one of a position and an orientation of the at least one tool;

a targeting system including a base and a tube extending upwardly from a geometric center of the base, the base being stationary with respect to the patient and being mounted over the single surgical port, the tube being pivotable with respect to the base and being configured to receive each of the probes and the sheath therein, wherein each of the probes is inserted into the single surgical port and through the base; and at least one controller configured to i) manipulate at least a portion of one of the series of interchangeable probes to treat the target volume ii) track the at least one tool in real-time, and iii) display the position of the at least one tool on a screen, wherein the at least one controller monitors a position and orientation of the sheath such that the probes are inserted and removed from the sheath while maintaining a desired orientation of all of the probes along a same or substantially same trajectory into and out of the sheath.

13. The system according to claim 12, further comprising:
a robot containing the at least one motor, the robot connecting the series of interchangeable probes to the at least one motor.

14. The system of claim 12, wherein the at least one sensor includes intra-tissue ultrasound to provide visualization of an interior of the target volume, and wherein the at least one sensor includes fiber optics to provide visualization of an exterior of the target volume.

* * * * *